United States Patent [19]

Hoult

[11] Patent Number: 5,023,804
[45] Date of Patent: Jun. 11, 1991

[54] METHOD AND APPARATUS FOR COMPARING SPECTRA

[75] Inventor: Robert A. Hoult, Bethel, Conn.
[73] Assignee: The Perkin-Elmer Corporation, Norwalk, Conn.
[21] Appl. No.: 355,587
[22] Filed: May 23, 1989
[51] Int. Cl.$^5$ .............................. G01J 3/42
[52] U.S. Cl. ............... 364/498; 364/497; 356/303; 356/319
[58] Field of Search .......... 364/497, 498, 525, 571.01; 356/300, 303, 319, 326; 324/307, 311, 312, 316

[56] References Cited

U.S. PATENT DOCUMENTS

| | | | |
|---|---|---|---|
| 4,238,830 | 12/1980 | Unyala | 364/573 |
| 4,365,303 | 12/1982 | Hannah et al. | 364/498 |
| 4,560,275 | 12/1985 | Goetz | 356/326 |
| 4,692,883 | 9/1987 | Nelson et al. | 364/497 |
| 4,710,024 | 12/1987 | Fukuma | 364/498 |
| 4,726,679 | 2/1988 | McCaffrey | 356/315 |
| 4,744,657 | 5/1988 | Aralis et al. | 364/498 |
| 4,766,551 | 8/1988 | Begley | 364/498 |
| 4,801,209 | 1/1989 | Wadlow | 364/498 |
| 4,807,148 | 2/1989 | Lacey | 364/498 |
| 4,824,249 | 4/1989 | Lucas et al. | 364/498 |

OTHER PUBLICATIONS

"Computer Retrieval of Infrared Spectra by a Correlation Coefficient Method", by K. Tanabe and S. Saeki, *Anal. Chem.*, vol. 47, No. 1, Jan. 1975, pp. 118–122.
"Digital Filter for Computationally Efficient Smoothing of Noisy Spectra", by M. U. A. Bromba and H. Ziegler, *Anal. Chem.*, pp. 1299–1302, Mar. 1983.
"The Development of the Model 1600 FT-IR Spectrophotometer", by R. A. Hoult, Perkim Elmer Tech. Notes, Jan. 1989, pp. 4–13.

*Primary Examiner*—Parshotam S. Lall
*Assistant Examiner*—Brian M. Mattson
*Attorney, Agent, or Firm*—H. S. Ingham; E. T. Grimes

[57] ABSTRACT

In a method and a system for analyzing spectral data including a spectrophotometer and a spectral detector, a data station receives first transmittance spectrum data points and has a file register containing second transmittance spectrum data points. The first and second transmittance data points are transformed respectively to set of first and second absorbance spectrum data points. The first and second absorbance points are band pass filtered at a characteristic frequency nominally associated with spectral bandwidth so as to produce respective sets of first and second filtered data points. A set of weighting factors are established, each corresponding to the square of the sum of a first transmittance point and a second transmittance point for a selected frequency. A comparison factor is generated as a normalized sum of products over a selected spectral frequency range, each product being formed of a weighting factor and corresponding first and second absorbance data points for each selected spectral frequency.

10 Claims, 3 Drawing Sheets

METHOD AND APPARATUS FOR COMPARING SPECTRA

The present invention relates to the comparison of spectra, and particularly to the digital weighting of spectral data in the computation of a comparison factor. The invention is particularly adapted, among other possible uses, for use with an infrared spectrophotometer. This application is related to Applicants' U.S. Pat. No. 4,974,209 issued on Nov. 27, 1990.

BACKGROUND OF THE INVENTION

Modern spectrophotometers are providing greatly enhanced performance in terms of speed and accuracy by means of digital processing of the spectral data. A typical purpose is to provide a comparison of one spectrum with another spectrum or with each spectrum of a set of other spectra. For example, a sample being tested with the spectrophotometer may supposedly be known, and it is desired to compare its spectrum with that of the known material to determine whether the supposition is correct or the sample contains impurities. Another purpose is to compare the sample spectrum with a library of spectra stored in the data station or on a disk that can be addressed. Comparisons may be made by visual observations of the spectra as taught in U.S. Pat. No. 4,560,275 (Goetz), but this method is not always sufficiently accurate nor is it quantitative.

The most common purpose of infrared spectral searching is to match the spectrum of a material to be identified with a spectrum in a library. Various techniques, including peak matching, peakintensity matching, correlation coefficient, Euclidean distance matching, and factor analysis have been applied to spectral searching in order to rapidly compare and rank comparisons of a spectrum to relatively large data sets or libraries. The use of a correlation coefficient is described in an article "Computer Retrieval of Infrared Spectra by a Correlation Coefficient Method" by K. Tanabe and S. Saeki, *Analytical Chemistry* 47, 118–122 (Jan. 1975).

Several problem phenomena interfere with accuracy of the comparison. These include random noise, instrumental artifacts such as electronic spikes, and drift from temperature changes. A further problem associated with the noise is detecting small differences between overlapping peaks. Filtering of spectra by computer algorithm is disclosed, for example, in an article "Digital Filter for Computationally Efficient Smoothing of Noisy Spectra" by M. U. A. Bromba and H. Ziegler, *Analytical Chemistry* 55, 1299–1302 (1983). Comparisons may be made on such filtered or smoothed spectra such as by subtracting data as disclosed in U.S. Pat. No. 4,365,303 (Hannah et al). However, it has been found that simple one-step filtering before comparing can be insufficient to reliably distinguish close spectra. Other examples of processing spectral data are found in U.S. Pat. No. 4,238,830 (Unvala).

Therefore, objects of the present invention include improved resolution in the treatment of spectral signals to provide an accurate comparison of spectra.

SUMMARY OF THE INVENTION

The foregoing and other objects are achieved by a method of analyzing spectral data from an analytical instrument including a spectrophotometer, a spectral detector and a data station having a microprocessor. The data station is receptive of spectral signals from the detector in the form of transmittance spectrum data points. The method comprises the steps of operating the instrument so as to generate and store first and second sets of transmittance spectrum data points for selected frequencies over a selected spectral frequency range, and establishing a set of weighting factors, each such factor being proportional to a sum of a first transmittance data point and a second transmittance data point for a selected frequency in the selected frequency range. The method further comprises transforming the first and second transmittance points respectively to sets of first and second absorbance spectrum data points, and converting at least one of the first and second sets of absorbance data points to a weighted data set by multiplying each data point in the at least one set by a corresponding weighting factor. The method further comprises comparing the first data set and the second weighting factor, comparing the first data set and the second data set over the selected spectral frequency range by utilizing the at least one weighted data set so as to generate a comparison factor, and displaying the spectral comparison factor.

According to a preferred aspect of the invention, wherein the first and second spectra each have at least one Lorentzian type band with a band width associated nominally with a characteristic periodicity in common, the step of selectively weighting comprises band pass filtering by microprocessor the first and second spectra about the characteristic frequency. Preferably the filtering comprises convoluting the first and second spectra.

The comparison factor advantageously is a normalized sum of products for each of a set of selected spectral frequencies over a selected spectral frequency range. Each product is formed of a weighting factor and corresponding first and second absorbance data points for a selected spectral frequency. The filtering is effected on the absorbance spectra prior to computation of the comparison factor.

The objects of the invention also are achieved with a processing system incorporated into the above-described analytical instrument comprising means for carrying out the steps of the foregoing method.

BRIEF DESCRIPTION OF THE DRAWINGS

FIGS. 2(*a*)–2(*c*) are sets of sample plots of spectra associated with the invention.

DETAILED DESCRIPTION OF THE INVENTION

Although it will be recognized by those skilled in the art that the concepts of the present invention can be used in other types of analytical instruments, the description herein is presented in conjunction with an infrared spectrophotometer. When subject to infrared radiation, each functional group of an organic molecule has associated absorption bands throughout a transmission spectrum. For a particular functional group, the absorption bands at certain wavelengths are specific, i.e. not the result of interferences, etc., and these bands provide are infrared "fingerprint" of the molecule.

The analytical instrument of the present invention (FIG. 1) may be considered as being composed of a spectrophotometer 10, detector means 12, a data station indicated generally at 14, a visual display unit 16 and a keyboard module 18. The spectrophotometer 10 may be of any suitable type such as, for example, Model 1600, manufactured by The Perkin-Elmer Corporation. This instrument utilizes a scanning Michelson interferometer and is described in an article "The Development of the Model 1600 FT-IR Spectrophotometer" by R. A. Hoult, *Perkin-Elmer Tech Notes* 1st quarter 1989. Communication between the operator and the data station 14 is accomplished via the keyboard 18. This keyboard contains, in addition to the standard terminal format, a number of special function keys which allow the operator to select a specific task from one of the application programs by depressing the appropriate key on the keyboard. The video screen 16 is used to display commands to be entered into the system by way of the keyboard 18, to show status and properties of data collected allow and to viewing of spectra. The screen may be used to display a spectrum directly during a scan and to display any of the computed spectral data which result after each step of data processing.

Figure 1:
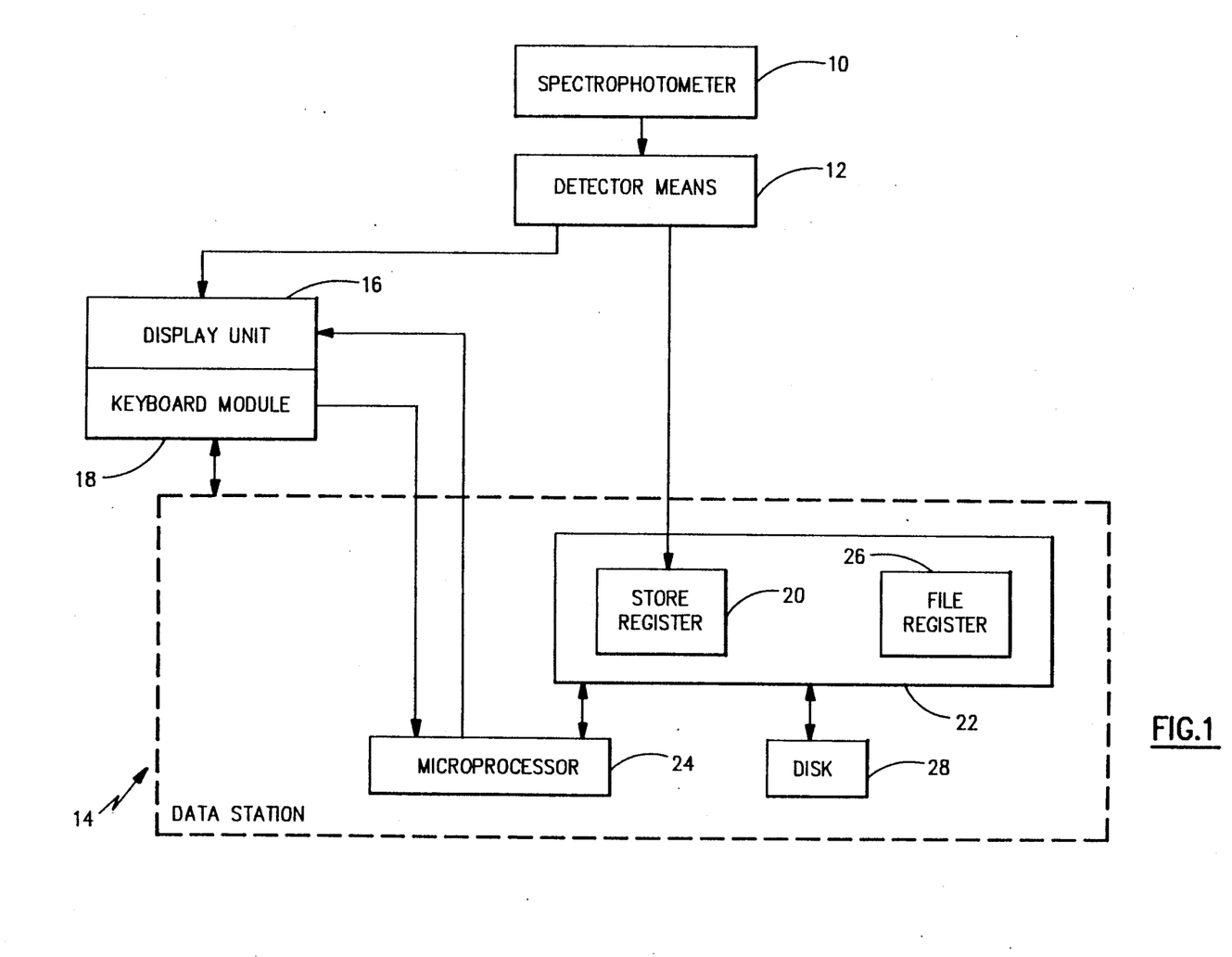
FIG. 1 is a block diagram of an analytical instrument for implementing the invention.

The data received from detector 12 is digitized conventionally and stored as a set of data points in a store register 20 which is part of a memory system 22 in the data station. When a comparison is desired an operator presses a "compare" button on keyboard 18. A further entry is made to select one or more available types of filtering and/or weightings as will become apparent below. An "execute" command commences computations in a microprocessor portion 24 of the data station. The microprocessor draws one set of transmittance spectrum data points from store register 20 and another set of transmittance spectrum data points from a file register 26 which, in turn, may receive its data from a disk 28 or previously from the store register. The computations filter, weight and compare two sets of spectral data from the store and file registers, as further described below.

Figure 2A:
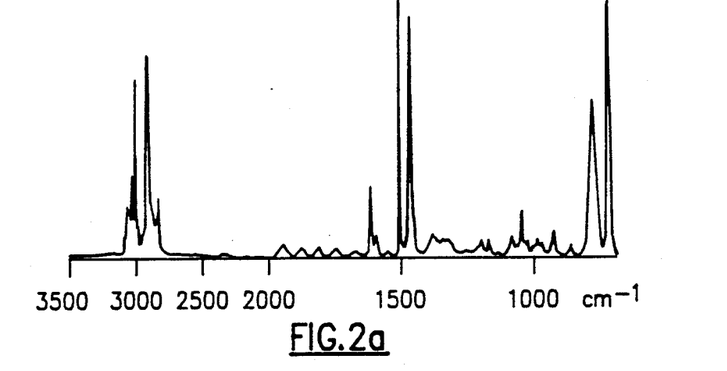

There are various ways that the two spectra may be compared, for example by computing the differences for each point along the spectral curve of transmittance vs. frequency or wave number. Advantageously, within the present invention, a scalar product is computed which is essentially a correlation coefficient. This product in the form of a Normalized Dot Product (NDP) is determined according to the formula:

$$NDP = \frac{\sum_i X_i \cdot Y_i}{\left[\sum_i X_i \cdot X_i \cdot \sum_i Y_i \cdot Y_i\right]^{\frac{1}{2}}}$$

where:

$X$ = data input point for first spectrum
$Y$ = data input point for second spectrum
$i$ = index of input points The summation is made over all i's which represent optical frequency or its equivalent in wave number increments, such as in steps of one wave number. Before making this computation, it is preferable first to transform the spectrum from transmittance to absorbance in a manner that makes the data independent of thickness or dilution of the sample in the spectrophotometer. This transformation is effected by computing absorbance as the negative logarithm (preferably base 10) of the transmittance for each point vs. wave number. The result, when displayed, is a generally horizontal line with absorption band peaks characteristic of the particular sample or material, as shown in FIG. 2a.

Further according to the invention, the data points for the two spectra are treated or weighted by a weight means. One preferred treatment of the spectral data involves filtering of the absorbance data to remove short and long periodicities. Such a resolution filter deweights short periodicity noise and also instrument baseline variation at long periodicities. Filtering of an analog spectrum may be effected by an electronic circuit with a low band pass filter, then converted to digital data. Advantageously according to the present invention, this is achieved by microprocessor computation in the data station, preferably by means of a one cycle triangular wave with a center value of zero.

The selected filter periodicity in wave number or wave length is associated with the spectral linewidths. (As used herein and in the claims, the terms "frequency" and "periodicity" also include corresponding wave number or wave length.) The spectra each are formed of at least one Lorentzian type spectral band with a typical natural band or line width in the infrared from about 8 to 16 cm$^{-1}$ (wavenumbers) for the majority of substances of interest (largely organic). Thus, the characteristic periodicity of the filter, corresponding to one cycle of the wave, is desirably selected as 16 cm$^{-1}$. Advantageously, the wave is a triangular wave, represented by a weight function which, with a wave length of 16, is:

$$0 \; -1 \; -2 \; -3 \; -4 \; -3 \; -2 \; -1 \; 0 \; +1 \; +2 \; +3 \; +4 \; +3 \; +2 \; +1$$

This filter is applied as a series of filter weights for a mid-point H of a range of neighboring points A through O representing spectral intensities over the filter wave length by computing a filtered point H':

$$H' = -A -2B -3C -4D -3E -2F -G +I +2J +3K +4L +3M +2N +O.$$

It will be appreciated that each point in the array would normally have to be calculated separately, which would require an enormous number of calculations including many multiplications. This would be very time consuming for a small computer. To avoid excessive multiplications, the algorithm is implemented using successive differences which represent the result of successive computations during indexing from low to high index number over the selected spectral range of wave numbers, derived as follows:

```
     -1  -2  -3  -4  -3  -2  -1   0  +1  +2  +3  +4  +3  +2  +1
 -(-1  -2  -3  -4  -3  -2  -1   0  +1  +2  +3  +4  +3  +2  +1)
     +1  +1  +1  +1  -1  -1  -1  -1  -1  -1  -1  -1  +1  +1  +1  +1
 -(+1  +1  +1  +1  -1  -1  -1  -1  -1  -1  -1  -1  +1  +1  +1  +1)
     -1   0   0   0  +2   0   0   0   0   0   0   0  -2   0   0  +1
```

In computing a succession of spectral data points, the results reduce to a simple set of expressions for modified computation of a generalized point $X_i'$:

$$SUM\ 0 = -X_{i-2n-1} + 2X_{i-n-1} - 2X_{i+n-1} + X_{i+2n-1}$$

$$SUM\ 1' = SUM\ 1 + SUM\ 0$$

$$X_i' = SUM\ 2' = SUM\ 2 + SUM\ 1$$

where:
  $X$ = data input point
  $i$ = index of output (filtered) point to be generated
  $n$ = quarter wave length of filter (4 in present example)
  SUM = summation
  0,1,2 = computations for prior point
  1',2' = current computations.

The computations are iterated successively through the spectral wave numbers, using prior computations starting with highest wave number. (An equivalent mode utilizes computations high to low index, interchanges + and − in the indexes of SUM 0 , and starts with the lowest wave number.) The first two computations at the beginning of the range may be effected direct computation, such as illustrated above for point H', in order to establish the first SUM 1. The modified computation substantially reduces the umber of calculation steps and is especially suitable for effecting with simple addition via an assembly program routine as follows:

| Program | |
|---|---|
| ***** stack parameter equates ***** | |
| * | |
| npts = 20 | |
| from = 24 | |
| to = 28 | |
| ***** resister usage ***** | |
| * | |
| * d0/d1 | work resisters |
| * d2/d3 | first difference |
| * d5/d6 | result |
| * d7 | points counter |
| * a0-a3 | input pointers |
| * a4 | output pointer |
| ***** subroutine diffilt ***** | |
| .text | |
| .even | |
| .slobl | -diffilt |
| -diffilt: | |
| * | |
| * save registers | |
| movem.1 | d3/d5/a3/a4,-(a7) |
| * set parameters | |
| movem.1 | npts(a7),d7/a0/a4 |
| * | |
| ** compute first output point explicitly | |
| * decrement npts | |
| suba.w | #1,d7 |
| bcs | exit |
| * setup address pointers | |
| lea | 32(a0),a3 |
| lea | 4(a0),a2 |
| move.1 | a0,a1 |
| lea | −28(a0),a0 |
| * sum weights of 1 | |
| move.1 | −(a3),d6 |
| add.1 | (a2)+,d6 |
| slt | d5 |
| move.1 | −(a1),d1 |
| add.1 | (a0)+,d1 |

| Program | |
|---|---|
| slt | d0 |
| sub.1 | d1,d6 |
| subx.b | d0,d5 |
| * sum weights of 2 | |
| move.1 | −(a3),d3 |
| add.1 | (a2)+,d3 |
| slt | d2 |
| move.1 | −(a1),d1 |
| add.1 | (a0)+,d1 |
| slt | d0 |
| sub.1 | d1,d3 |
| subx.b | d0,d2 |
| add.1 | d3,d6 |
| addx.b | d2,d5 |
| add.1 | d3,d6 |
| addx.b | d2,d5 |
| * sum weights of 3 | |
| move.1 | −(a3),d3 |
| add.1 | (a2)+,d3 |
| slt | d2 |
| move.1 | −(a1),d1 |
| add.1 | (a0)+,d1 |
| slt ! | d0 |
| sub.1 | d1,d3 |
| subx.b | d0,d2 |
| add.1 | d3,d6 |
| addx.b | d2,d5 |
| add.1 | d3,d6 |
| addx.b | d2,d5 |
| add.1 | d3,d6 |
| addx.b | d2,d5 |
| * sum weights of 4 | |
| move.1 | (a2),d1 |
| sub.1 | (a0),d1 |
| slt | d0 |
| add.1 | d1,d1 |
| addx.b | d0,d0 |
| add.1 | d1,d1 |
| addx.b | d0,d0 |
| add.1 | d1,d6 |
| addx.b | d0,d5 |
| * scale and output result | |
| move.1 | d6,d1 |
| move.b | d5,d0 |
| and.b | #0x1f,d0 |
| and.b | #0xe0,d1 |
| or.b | d0,d1 |
| ror.1 | #5,d1 |
| move.1 | d1,(a4)+ |
| * | |
| ** compute first difference explicitly | |
| * decrement npts | |
| subq.w | #1,d7 |
| bcs | exit |
| * setup address pointers | |
| move.1 | from(a7),a0 |
| lea | 36(a0),a3 |
| lea | 20(a0),a2 |
| lea | −12(a0),a1 |
| lea | −28(a0),a0 |
| * loop initialisation | |
| moveq | #0,d3 * clear accumulator |
| moveq | #0,d2 |
| swap | d7 * save counter |
| move.w | #3,d7 |
| ** summation loop | |
| 11: move.1 | −(a3),d1 |
| add.1 | (a0)+,d1 |
| slt | d0 |
| add.1 | d1,d3 |
| addx.b | d0,d2 |
| move.1 | −(a2),d1 |
| add.1 | (a1)+,d1 |
| slt | d0 |
| sub.1 | d1,d3 |
| subx.b | d0,d2 |
| dbra | d7,11 |
| swap | d7 * retrieve counter |
| * | |
| * initialise main filter address resisters | |
| move.1 | from(a7),a0 |

-continued

| | Program | |
|---|---|---|
| | lea | 36(a0),a3 |
| | lea | 20(a0),a2 |
| | lea | −12(a0),a1 |
| | lea | −28(a0),a0 |
| *** | main filter loop | |
| bra.s | 12 | * start the loop in the middle |
| loop: | | |
| * | compute first difference | |
| | move.l | (a0)+,d1 |
| | sub.l | (a3)+,d1 |
| | slt | d0 |
| | sub.l | d1,d3 |
| | subx.b | d0,d2 |
| | move.l | (a1)+,d1 |
| | sub.l | (a2)+,d1 |
| | slt | d0 |
| | add.l | d1,d1 |
| | addx.b | d0,d0 |
| | add.l | d1,d3 |
| | addx.b | d0,d2 |
| * | compute result | |
| 12: | add.l | d3,d6 |
| | addx.b | d2,d5 |
| * | scale and output result | |
| | move.l | d6,d1 |
| | move.b | d5,d0 |
| | and.b | #0x1f,d0 |
| | and.b | #0xe0,d1 |
| | or.b | d0,d1 |
| | ror.l | #5,d1 |
| | move.l | d1,(a4)+ |
| ** | end of loop | |
| | dbra | d7,loop |
| ** | exit | |
| exit: | | |
| * | restore resisters and return | |
| | movem.l | (a7)+,d3/d5/a3/a4 |
| | rts | |

Figure 2B:
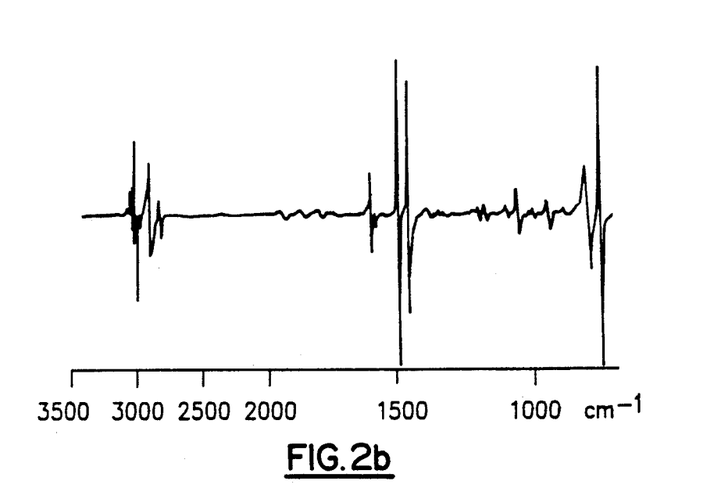

A filtered data set is essentially a convoluted spectrum as may be seen in FIG. 2b (obtained from the absorbance spectrum of FIG. 2a), having the appearance of first derivatives of the peaks with the noise considerably suppressed. However, remaining noise at these convoluted peak locations may be higher than in other parts of the spectrum for the following reason. In a typical spectrometer, the noise is substantially independent of the signal. As a result, the noise is a larger proportion of low transmittance signals than of high transmittance signals. When converted to absorbance, the spectrum, herefore, appears noisy in regions of higher absorbance, that is, where the spectrum peaks normally are found. Therefore, further weighting factors are utilized in the invention to deweight the data at the peaks, and utilized in the invention to deweight the data at the peaks, and to emphasize the off-peak data including the peak sides.

The further weighting factors, also herein termed "transmittance weighting", are based on the average of the first and second transmittance data points for the first and second spectra, i.e. for the sample and comparison (file) spectra. Thus, a weighting factor for a specified peak with wave number index i is $W_i = T_{1i} + T_{2i}$, where T are the respective transmittances. Preferably, the weighting factors are squared, thus weighting each of the first and second data points, effectively converting each of the first and second absorbance data points respectively to a first and second weighted data set. A correlation coefficient in the form of a Weighted Normalized Dot Product (WNDP) is then computed as:

$$WNDP = \frac{\sum_i W_i^2 \cdot X_i \cdot Y_i}{\left[ \sum_i W_i^2 \cdot X_i \cdot X_i \cdot \sum_i W_i^2 \cdot Y_i \cdot Y_i \right]^{\frac{1}{2}}}$$

This gives low weight wherever two strong absorbencies coincide since average transmittance is low there, so relatively higher weighting in the peak sides contributes more to the correlation coefficient. Also, the weighted correlation coefficient tends to emphasize differences between the spectra rather than identities which is an important object of the present invention.

Typically, instrument noise is minimal in the spectral range where radiation maximizes at the, instrument source temperature, i.e. around 2500 cm$^{-1}$ wave number (4 microns).

An advantageous modification to the weighting factors is effected by the multiplication of the average transmittances for each wave number by a black body factor (BBF) such as may be defined by the conventional black body formula:

$$BBF = C f^3 (e^{hf/kt} - 1)^{-1}$$

where f is frequency, T is Temperature and C, h and k are well known constants.

Temperature is taken as 1080° C. This formula is itself not critical and any other formula that gives similar weighting may be used. However, the black body curve is a convenient correction. As used herein and in the claims, "black body factor" denotes the above or any similar weighting formula. The modified weighting factor is used to correct the correlation coefficient as explained above.

Figure 2C:
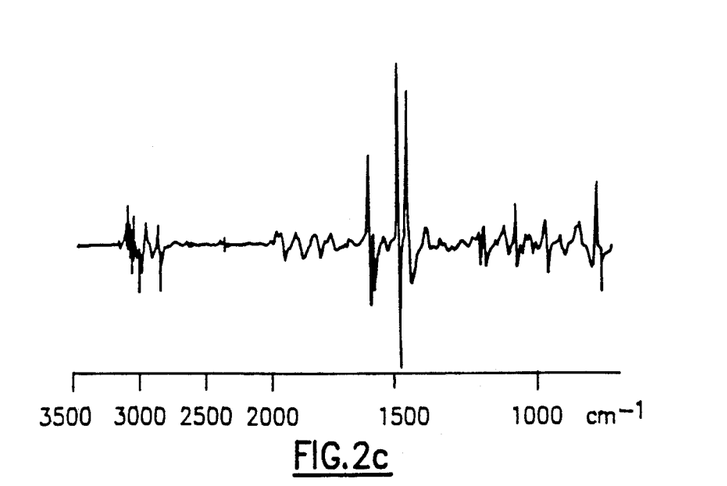

FIG. 2c illustrates the result of convolving, filtering, transmittance weighting and black body correction on the spectrum of FIG. 2b. The spectral features at the low and high frequency ends of the spectrum are reduced in magnitude, and the relative band intensity of weak bands to the strong bands is enhanced. Carbon dioxide is always present in air in varying amounts depending on local conditions such as breathing personnel. For ease, low cost and high speed of operation, a sample is placed in a spectrophotometer chamber open to atmosphere. Since the carbon dioxide produces peaks of unpredictable height in the spectra, the weighting factors are deweighted to zero in narrow bands at any one or more of spectral frequencies in the range corresponding to the carbon dioxide absorption frequencies. The usual wave numbers suppressed are from 660 to 674 cm$^{-1}$ and from 2280 to 2390 cm$^{-1}$.

Water vapor may also be a similar problem but has bands at wave numbers of interest for the comparisons. Therefore, optionally, a similar but partial deweighting may be effected, such as by a factor of eight at wave numbers of 1300 to 1900 cm$^{-1}$ and 3500 to 4000 cm$^{-1}$.

Finally, noise was determined to remaining be a problem for tall sharp peaks. This particular noise is eliminated by computational means such that whenever the weighting factor $T_{1i} + T_{2i}$ falls below a threshold near zero, the weight is set to zero, and the zero is spread to the half width of the filter, i.e. 8 cm$^{-1}$ This completely eliminates wings of noise spreading from the tips of these peaks by the resolution weighting filter.

Figure 3:
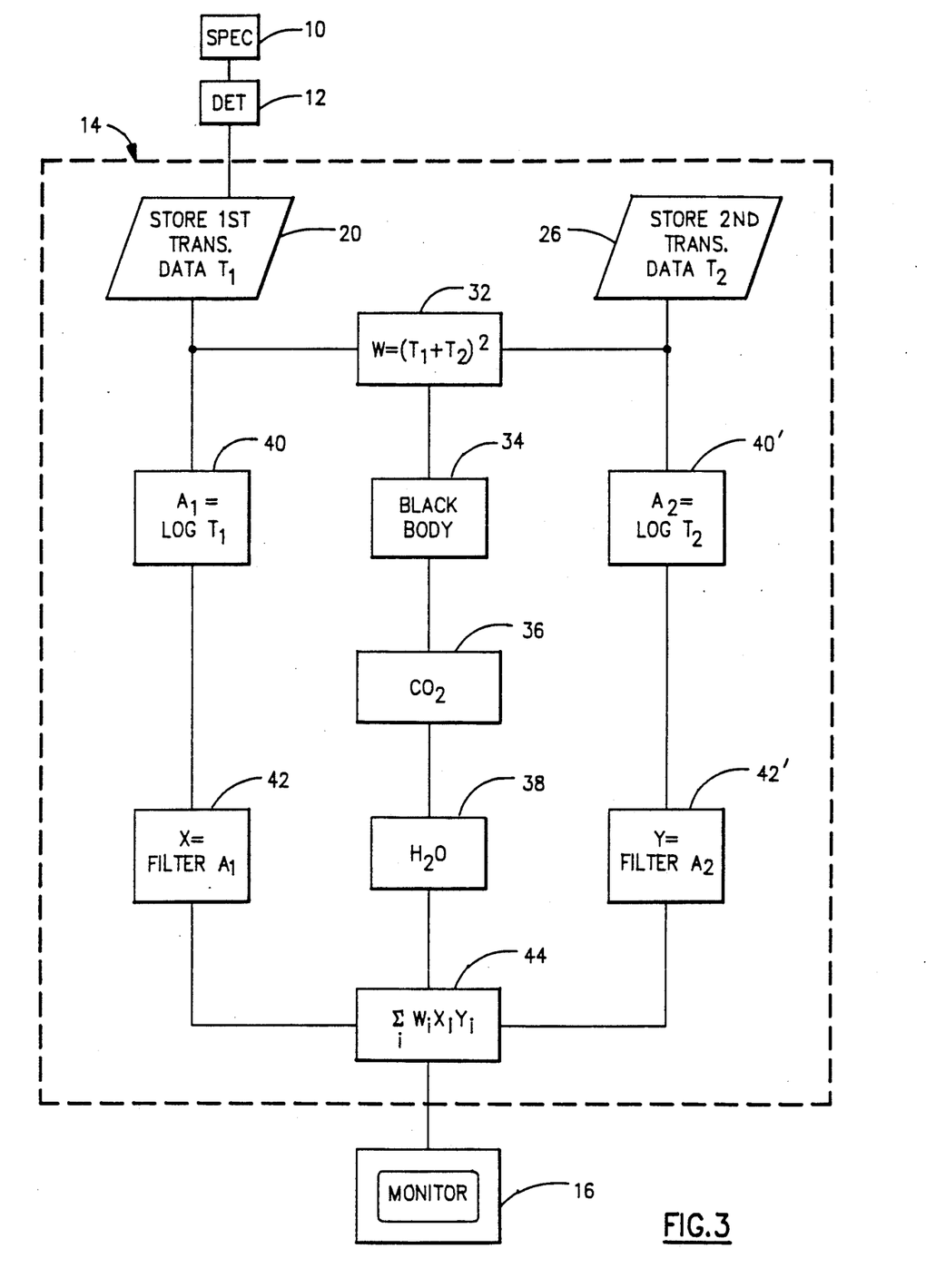
FIG. 3 is a flowchart illustrating the invention.

FIG. 3 is a flowchart summarizing the aforedescribed steps, and also serves to indicate the arrangement of components in the analytical instrument according to the invention. The processing components may be individual sections of electronic circuitry or parts of a software program. Spectrophotometer 10 provides spectra to detector 12 which in turn sends spectral signals to the first storage register 20 in data station 14, retaining the first transmittance spectrum data points. Second storage register 26 has stored therein the second transmittance spectrum data points.

The transmittance points are added and the sum is squared in the weight means 32. Optionally, the resulting weighting factors are modified with respective weighting for black body 34, carbon dioxide 36 and/or water 38. Separately each set of transmittance points are transformed by the transform means 40,40', such as by the utilization of logarithms, to absorbance spectrum data points. These points then are treated by the filter 42,42' means to generate the filtered data points.

The three sets of information are brought together in the compare means 44 for generating the normalized sum of products of the modified weighting factor and the filtered data points, said sum being the correlation coefficient. The latter is presented in the display 16, which is either a monitor screen or a printout, and saved or combined with other data runs as desired. The effects of various filtering and weighting combinations on the ability to discriminate between apparently similar spectra are presented in Table 1. Ten spectra of neat p-xylene and ten spectra of 0.775% m-xylene in p-xylene were compared against the average of twenty-five spectra of neat p-xylene. The weighting and filter combinations are described in the table. A Discrimination Factor (DF) is:

$$DF = \frac{3(s_a + s_b)}{r_a - r_b}$$

where $s_a$ and $s_b$ are the standard deviations, and $r_a$ and $r_b$ are the correlations of the neat and mixture spectra, respectively. The discrimination factor approaches zero as the standard deviation becomes small or the correlation difference approaches one.

TABLE 1

Effect of filter and weight combinations on the discrimination of similar spectra.

| Filter Weight | $r_a$ | $s_a$ | $r_b$ | $s_b$ | DF |
|---|---|---|---|---|---|
| 0 | 0.999846 | 0.0000083 | 0.999960 | 0.0000047 | 18.52 |
| 2 | 0.999775 | 0.000171 | 0.999838 | 0.000187 | 21.86 |
| 4 | 0.999999 | 0 | 0.999990 | 0.0000220 | 7.33 |
| 8 | 0.999852 | 0.000175 | 0.999788 | 0.000187 | 16.96 |
| 16 | 0.999846 | 0.00171 | 0.999788 | 0.000187 | 18.51 |
| 2 + 4 | 0.999983 | 0.0000034 | 0.999953 | 0.0000111 | 1.449 |
| 2 + 8 | 0.999775 | 0.000282 | 0.999738 | 0.000326 | 49.28 |
| 4 + 8 | 0.999999 | 0 | 0.999990 | 0.0000219 | 7.300 |
| 2 + 4 + 8 | 0.999984 | 0.0000033 | 0.999960 | 0.0000047 | 0.9991 |

Filter

TABLE 1-continued

Effect of filter and weight combinations on the discrimination of similar spectra.

| Weight | Definition |
|---|---|
| 0 | No weighting or convolving |
| 2 | Convolved (resolution weighting) |
| 4 | Transmittance weighting plus black body |
| 8 | $CO_2$ bands suppressed |
| 16 | $H_2O$ regions de-weighted |

As seen in Table 1, the combination of resolution filtering, transmission weighting, black body and carbon dioxide suppression provides a resolution of approximately three standard deviations. Variations in atmospheric carbon dioxide, even in an interleaved background collection, are sufficient to reduce separation from three standard deviations to approximately two standard deviations resolution. Omission of either the transmission weighting with black body weighting or the resolution weighting make the discrimination impossible for this example. However, in other circumstances, filtering or transmission weighting may be satisfactory, and the data station/keyboard allows individual or combination selections.

TABLE 2

Comparison of m-xylene/p-xylene mixtures versus averaged spectrum of neat p-xylene with 2 + 4 + 8 (normal) filtering.

| m-xylene/p-xylene (%) versus p-xylene reference | average correlation | standard deviation reference | discrimination from p-xylene |
|---|---|---|---|
| 0.775 | 0.999960 | 0.0000047 | 0.997 |
| 1.46 | 0.999903 | 0.0000058 | 0.344 |
| 2.58 | 0.999748 | 0.0000094 | 0.165 |

Although a normalized sum (correlation coefficient) is highly advantageous as comparison factor for comprising spectra, other comparison factors may be substituted or additionally computed. One such useful factor is, for example, a weighted Euclidian distance $[1-(WNDP)2]^{\frac{1}{2}}$.

As indicated above, assembly language is desirable for implementing the present invention, a program being provided herein for the filtering aspect. Those skilled in the art will be able to program other aspects of the invention by following the outlines provided herein. Other computer languages may, of course, be utilized to the extent allowed by the particular data station and microprocessor in use.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. A method of analyzing spectral data from an analytical instrument including a spectrophotometer, a spectral detector receptive of spectra from the spectrophotometer, and a data station receptive of transmittance spectrum data points from the detector; the method comprising the steps of:

operating the instrument so as to generate and store first and second sets of transmittance spectrum data points for selected frequencies over a selected spectral frequency range;

establishing a set of weighting factors, each such factor being proportional to a sum of a first transmittance data point and a second transmittance data point for a selected frequency in the selected frequency range;

transforming of the first and second transmittance points respectively to sets of first and second absorbance spectrum data points;

converting at least one of the first and second sets of absorbance data points to a weighted data set by multiplying each data point in the at least one set by a corresponding weighting factor;

generating a spectral comparison factor as a normalized sum of products for each selected frequency range, each product being formed of a weighting factor squared and corresponding first and second unweighted absorbance data points; and displaying the spectral comparison factor.

2. The method according to claim 1 wherein the absorbance data points are generated as a logarithm of the corresponding transmittance data points.

3. The method according to claim 1 wherein each weighting factor is further proportional to a black body factor having a value according to the corresponding selected spectral frequency.

4. The method according to claim 1 wherein the weighting factors are equated to zero in a narrow band at a spectral frequency corresponding to carbon dioxide spectral absorption.

5. The method according to claim 1 wherein each of the spectra is formed of at least one spectral band with a typical band width corresponding to a characteristic periodicity, and the method further comprises the steps of, prior to the steps of converting and comparing, band pass filtering the first absorbance data points about the characteristic periodicity.

6. The method according to claim 5 wherein the step of filtering comprises convoluting the first and second absorbance spectra.

7. The method according to claim 6 wherein the step of convoluting comprises filter weighting each of a succession of selected absorbance data points of the first and second spectra with a one cycle triangular wave having the characteristic periodicity and a zero crossing substantially at each selected data point.

8. The method according to claim 7 wherein the triangular wave consists of a series of filter weights, and the first and second filtered data sets consist of output data points each computed as a filter weighted sum of products of neighboring spectral data points and corresponding filter weights.

9. The method according to claim 8 wherein the first and second filtered data sets consist of output data points $X_i'$ each computed by a formula:

$$SUM\ 0 = -X_{i-2n-1} + 2X_{i-n-1} - 2X_{i+n-1} + X_{i+2n-1}$$

$$SUM\ 1' = SUM\ 1 + SUM\ 0$$

$$X_i' = SUM\ 2' = SUM\ 2 + SUM\ 1$$

where:
- $X$ = data input point
- $i$ = index of output (filtered) point to be generated
- $n$ = quarter wave length of filter (4 in present example)
- SUM = summation
- 0,1,2 = computations for prior point
- 1',2' = current computations.

10. A method of analyzing spectral data from an analytical instrument including a spectrophotometer, a spectral detector receptive of spectra from the spectrophotometer, and a data station receptive of spectral signals comprising transmittance spectrum data points from the detector, each of the spectra is formed of at least one spectral band with a typical bandwidth corresponding to a characteristic periodicity; the method comprising the steps of:

operating the instrument so as to generate and store first and second sets of transmittance spectrum data points for selected frequencies over a selected spectral frequency range;

establishing a set of weighting factors, each such factor being proportional to a square of a sum of a first transmittance data point and a second transmittance data point for a selected frequency in the selected freuqency range, and being further proportional to a black body factor having a value according to the corresponding selected spectral frequency;

generating first and second absorbance spectrum data points for each as a logarithm of the corresponding first and second transmittance data points;

filter weighting each of a succession of selected absorbance data points of the first and second spectra with a one cycle triangular wave having the characteristic periodicity and a zero crossing substantially at each selected data point, thereby generating respective first and second filtered data points;

generating a spectral comparison factor as a normalized sum of products for each selected frequency, each product being formed of a weighting factor squared and corresponding first and second filtered data points; and displaying the spectral comparison factor.

* * * * *

UNITED STATES PATENT OFFICE
CERTIFICATE OF CORRECTION

Patent No. 5,023,804                     Dated  June 11, 1991

Inventor(s)   Robert A. Hoult

It is certified that error appears in the above-identified patent and that said Letters Patent is hereby corrected as shown below:

In column 8, line 18, before "radiation" insert --black body--.

In column 8, line 61, change "to remaining be a" to --to be a remaining--.

In column 12, line 1, change "8" to --7--.

In column 12, lines 13-14, delete "(4 in present example)".

Signed and Sealed this

Twenty-seventh Day of April, 1993

*Attest:*

MICHAEL K. KIRK

*Attesting Officer*                    *Acting Commissioner of Patents and Trademarks*